United States Patent [19]
Lee

[11] Patent Number: 5,795,729
[45] Date of Patent: Aug. 18, 1998

[54] REDUCTIVE, ENERGY-TRANSFER FLUOROGENIC PROBES

[75] Inventor: Linda G. Lee, Palo Alto, Calif.

[73] Assignee: Biometric Imaging, Inc., Mountain View, Calif.

[21] Appl. No.: 597,018

[22] Filed: Feb. 5, 1996

[51] Int. Cl.$^6$ .............. C12Q 1/37; C12Q 1/26; C12Q 1/00; G01N 33/53
[52] U.S. Cl. .............. 435/24; 435/23; 435/25; 435/18; 435/4; 435/68.1; 435/968; 536/24.3; 252/582; 252/583
[58] Field of Search .............. 435/24, 23, 4, 435/25, 68.1, 968, 18; 252/582, 583; 536/24.3

[56] References Cited

U.S. PATENT DOCUMENTS

| | | | |
|---|---|---|---|
| 4,318,981 | 3/1982 | Burd et al. | 435/24 |
| 4,699,876 | 10/1987 | Libeskind | 435/24 |
| 4,910,300 | 3/1990 | Urdea et al. | 536/287 |
| 5,470,705 | 11/1995 | Grossman et al. | 435/6 |

FOREIGN PATENT DOCUMENTS

| | | |
|---|---|---|
| 0070685 | 1/1983 | European Pat. Off. |
| 0070687 | 1/1983 | European Pat. Off. |

OTHER PUBLICATIONS

Leventhal, et al., *Insulin-like Growth Factor-II as a Paracrine Growth Factor in Human Neuroblastoma Cells*, Experimental Cell Research 221; pp. 179–186 (1995).

Scudiero, et al., *Evaluation of a Soluble Tetrazolium/Formazan Assay for Cell Growth and Drug Sensitivity in Culture Using Human and other Tumor Cell Lines*, Sep. 1, 1988; Cancer Research; pp. 4827–4833.

Cory, et al., *Use of an Aqueous Soluble Tetrazolium/Formazan Assay for Cell Growth Assays in Culture*, Cancer Communications, vol. 3, No. 7, 1991, pp. 207–212.

Paull, et al. *The Synthesis of XTT: A New Tetrazolium Reagent that is Bioreducible to a Water-Soluble Formazan*, Jun. 1988, pp. 911–914.

Haugland, *Detecting Enzymatic Activity in Cells Using Fluorogenic Substrates*, Biotechnic & Histochemistry, vol. 70, No. 5, 1995, pp. 243–251.

Barltrop, et al., *5-(3-Carboxymethoxyphenyl)-2-(4, 5-Dimethylthiazolyl)-3-(4-Sulfophenyl) Tetrazolium, Inner Salt (MTS) and Related Analogs of 3-(4,5-Dimethylthiazolyl(-2,5-Diphenyltetrazolium Bromide (MTT) Reducing to Purple Water-Soluble Formazans as Cell-Viability Indicators*, Bioorganic & Medical Chemistry Letters, vol. 1, No. 11, pp. 611–614, 1991.

*Primary Examiner*—Louise N. Leary
*Attorney, Agent, or Firm*—Fulwider Patton Lee & Utecht, LLP

[57] ABSTRACT

An energy transfer fluorescent probe for detecting a reagent is provided which includes a fluorescent reporter molecule and a quencher molecule positioned on the probe relative to the reporter molecule such that the quencher molecule quenches the fluorescence of the reporter molecule when in a first state, the quencher molecule being converted by the reagent to a second state which has a reduced ability to quench the reporter molecule. Examples of conversions of the quencher molecule from a first state to a second state include reductions, oxidations, hydrolyses, phosphate cleavages, and the conversion of amides to amines. In one embodiment, the quencher molecule is a substrate for an enzyme which converts the quencher from a first state to a second state. For example, the enzyme may be an reductase, an oxidase, hydrolytic, a peptidase or a phosphorylase. The probe is used to fluorescently detect a reagent in a sample. According to the method, the probe is contacted with the sample containing the reagent wherein the quencher molecule is converted by the reagent from a first state which is able to quench the fluorescence of the reporter molecule to a second state which has a reduced ability to quench the reporter molecule. The reagent is detected by monitoring the fluorescence intensity of the reporter molecule as the quencher molecule is converted from the first state to the second state by the reagent.

30 Claims, 3 Drawing Sheets

REDUCTIVE, ENERGY-TRANSFER FLUOROGENIC PROBES

FIELD OF THE INVENTION

The present invention relates to fluorescent probes. More specifically, the present invention relates to fluorescent probes which include an energy transfer mechanism between a fluorescent reporter molecule and a quencher molecule.

BACKGROUND OF THE INVENTION

A variety of fluorescent probes have been developed for monitoring enzyme activity. In general, these probes serve as a substrate for the enzyme being detected and increase in fluorescent intensity when modified by the enzyme, the resulting change in fluorescence intensity being used to quantify the enzymatic activity.

One type of fluorescent probe relies on an energy transfer mechanism between a reporter molecule and a quencher molecule. This type of fluorescent probe has been used to detect protease or nuclease activity and generally includes an amino acid sequence or a nucleic acid sequence, a fluorescent reporter molecule and a molecule capable of quenching the fluorescence of the reporter molecule (hereinafter referred to as a quencher molecule). The quencher molecule is positioned on the probe such that the quencher molecule is able to quench the reporter molecule. As a result, the reporter molecule on the probe exhibits a lower average fluorescent intensity than reporter molecules which are not attached to the probe.

Protease and nuclease enzyme activities have been detected using these probes containing by measuring a change in fluorescence caused by the probe being digested by the protease or nuclease. When the enzyme digests the amino acid sequence or nucleic acid sequence, the reporter molecule or quencher molecule is released from the probe. This causes the reporter molecule and quencher molecule to become separated from each other, resulting in an increase in the fluorescence intensity of reporter molecules in the sample.

Probes containing a reporter - quencher molecule pair have been used to monitor a variety of biological reactions. For example, probes containing fluorescence-quencher pairs have been developed for monitoring amplification reactions, especially polymerase chain reactions (PCR). In these probes, the reporter molecule and quencher molecule are positioned on the probe sufficiently close to each other such that whenever the reporter molecule is excited, the energy of the excited state nonradiatively transfers to the quencher molecule where it either dissipates nonradiatively or is emitted at a different emission frequency than that of the reporter molecule. During strand extension by a DNA polymerase, the probe anneals to the template where it is digested by the 5'→3' exonuclease activity of the polymerase. As a result of the probe being digested, the reporter molecule is effectively separated from the quencher molecule such that the quencher molecule is no longer close enough to the reporter molecule to quench the reporter molecule's fluorescence. Thus, as more and more probes are digested during amplification, the number of reporter molecules in solution increases, thus resulting in an increasing number of unquenched reporter molecules which produce a stronger and stronger fluorescent signal.

Probes containing a reporter molecule—quencher molecule pair have also been developed for hybridization assays where the probe forms a hairpin structure, i.e., where the probe hybridizes to itself to form a loop such that the quencher molecule is brought into proximity with the reporter molecule in the absence of a complementary nucleic acid sequence to prevent the formation of the hairpin structure. WO 90/03446; European Patent Application No. 0 601 889 A2. When a complementary target sequence is present, hybridization of the probe to the complementary target sequence disrupts the hairpin structure and causes the probe to adopt a conformation where the quencher molecule is no longer close enough to the reporter molecule to quench the reporter molecule. As a result, these probes exhibit an increased fluorescent signal when hybridized to a target sequence than when unhybridized.

Another type of fluorescent probe that has been developed for fluorescently monitoring enzyme activity relies on the enzymatic conversion of a molecule on the probe into a more highly fluorescent species. This type of fluorescent probe has been used to understand the function and regulation of enzymes in cells. For example, this type of probe has been used to localize enzyme activity in particular organelles, to differentiate among cell types, and to determine the integrity or health of cells. Haugland, *Biotechnic & Histochemistry* 70:5 243–251 (1995).

A variety of probes for monitoring enzymatic hydrolysis, peptidase activity, oxidation and phosphate cleavage have been developed. For example, numerous fluorogenic substrates for hydrolytic enzymes, such as β-galactosidase, β-glucuronidase and alkaline phosphatase have been developed. These probes are commonly esters or ethers of phenolic fluorophore: 7-hydroxy-4-methylcoumarin (β-methylumbelliferone) and its analogs, fluorescein and resorufin. Fluorescent probes have also been developed for peptidases. These probes are commonly amino acid or peptide-amides of fluorescent amines. Dihydroethidium, dihydrofluoresceins and dihydrorhodamines have also been used as probes for detecting oxidation enzymes, such as peroxidases. Phosphate cleaving enzymes have been detected using ELF™ reagents which yield a fluorescent precipitate after cleavage and are sold by Molecular Probes.

The sensitivity of assays used to measure enzyme activity using fluorescent probes is generally limited by the background noise associated with the fluorescent probe. In general, oxidation, hydrolysis and phosphate cleavage reactions are energetically favored reactions which can occur in the absence of enzymatic activity to catalyze the reactions. As a result, a high background noise can be associated with these types of fluorescent probes.

Reduction reactions are energetically disfavored and thus occur at a far slower rate, if at all, in the absence of a catalyst. As a result, the background noise associated with probes which measure reduction reactions is significantly lower than probes which measure other types of enzyme reactions.

A variety of tetrazolium salts, such as MTT and XTT, have been developed for calorimetrically monitoring reduction reactions. These tetrazolium salt dyes are enzymatically reduced from a colorless salt to a highly colored formazan derivative and have been used as cell viability indicators. Parsons, et al., *J. Heterocyclic Chem.* 25 911–914 (1988); Barltrop, et al., *Bioorganic & Medicinal Chemistry Letters* 11 611–614 (1991); Cory, et al., *Cancer Communications* 3:7 207-212 (1991); Scudiero, et al., *Cancer Research* 48 4827–4833 (1988); Leventhal, et al., *Experimental Cell Research* 221 179–186 (1995). In comparison to fluorogenic probes, colorimetric probes, such as the above-described tetrazolium salt dyes, have the disadvantage that background noise due to absorbance of light by compounds in the sample can reduce the signal-to-noise ratio achieved using these dyes. By contrast, biological samples do not generally fluoresce above 500 nm. As a result, fluorescent dyes provide a much better signal-to-noise ratio than calorimetric dyes. In addition, powerful lasers can be used to enhance the sensitivity achieved with fluorescent dyes. A need therefore exists for a fluorogenic probe useful for monitoring enzymatic reduction reactions.

The development of fluorogenic probes for detecting enzymatic reduction reactions is made difficult by the fact that existing fluorescent dyes are generally highly oxidized aromatic moieties which undergo irreversible bond breakage when further oxidized. As a result, it is generally not possible to further oxidize existing fluorescent dyes to produce a probe which will become more highly fluorescent when reduced.

A general need exists for fluorescent probes for monitoring reactions. In particular, a need exists for fluorescent probes that are useful for monitoring reduction reactions. A further need exists for fluorescent probes which may be used to monitor enzymatic reactions and the detection of enzyme activity.

SUMMARY OF THE INVENTION

An energy transfer fluorescent probe for detecting a reagent is provided which includes a fluorescent reporter molecule and a quencher molecule positioned on the probe relative to the reporter molecule such that the quencher molecule is able to quench the fluorescence of the reporter molecule when in a first state, the quencher molecule being converted by the reagent to a second state which has a reduced ability to quench the reporter molecule.

Examples of conversions of the quencher molecule from a first state to a second state include reductions, oxidations, hydrolyses, phosphate cleavages, and the conversion of amides to amines.

In one embodiment, the quencher molecule is a substrate for an enzyme which converts the quencher from a first state to a second state. For example, the enzyme may be a reductase, an oxidase, a hydrolytic enzyme, a peptidase or a phosphatase.

In one embodiment, the quencher molecule has an absorbance maximum of between about 600 and 700 nm. In another embodiment, the absorbance maximum of the quencher molecule is within about 150 nm of the absorbance maximum of the reporter molecule. In one embodiment, the probe includes at least two quencher molecules. In another embodiment, the probe includes one or more reporter molecules and quencher molecules where the ratio of quencher molecules to reporter molecules on the probe is at least 2:1.

Examples of reporter molecules which may be used with the probe include fluorescien, rhodamine and cyanine dyes.

Examples of quencher molecules which may be used with the probe include dichloroindophenol and methylene blue.

The probe may include a variety of linkers for linking the reporter molecule to the quencher. Examples of linkers which may be used in the probes include alkyl groups, glycols, ethers, polyethers, polynucleotides, and polypeptides.

A method is also provided for fluorescently detecting a reagent in a sample using a probe of the present invention. The method includes contacting a fluorescent probe including a reporter molecule and a quencher molecule with a sample containing the reagent, the quencher molecule being converted by the reagent from a first state which is able to quench the fluorescence of the reporter molecule to a second state which has a reduced ability to quench the reporter molecule. According to the method, the fluorescence intensity of the reporter molecule is monitored as the quencher molecule is converted from the first state to the second state by the reagent.

In one embodiment of the method, the reagent is an enzyme. According to this embodiment, the method is conducted by contacting the fluorescent probe with a sample containing an enzyme, the quencher molecule being converted by the enzyme from a first state which is able to quench the fluorescence of the reporter molecule to a second state which has a reduced ability to quench the reporter molecule. Meanwhile, the fluorescence intensity of the reporter molecule is monitored as the quencher molecule is converted from the first state to the second state by the enzyme.

According to another embodiment of the method, the generation of a reagent by a chemical process is monitored. According to this embodiment, the fluorescent probe is introduced into a vessel in which the chemical process is performed. During the chemical process, the quencher molecule is converted from the first state to the second state as the reagent is formed during by the process.

DETAILED DESCRIPTION OF THE PREFERRED EMBODIMENT

Figure 1:
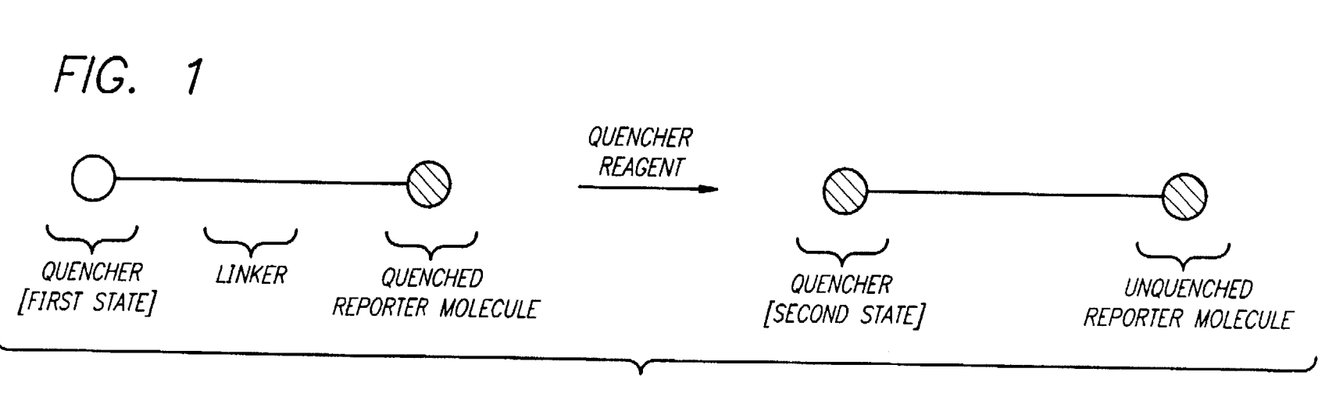
FIG. 1 illustrates a fluorescent probe according to the present invention which includes a reporter molecule, a quencher molecule and a linker linking the reporter molecule to the quencher molecule.

The present invention relates to a fluorescent probe for monitoring reactions which includes a fluorescent reporter molecule, a quencher molecule and a linker which links the fluorescent reporter molecule to the quencher molecule. The quencher molecule can adopt a first state where the quencher molecule is able to quench the fluorescence of the reporter molecule and a second state where the quencher molecule has a reduced ability to quench the reporter molecule. As illustrated in FIG. 1, when the quencher is in the first state, the quencher molecule is able to quench the fluorescence of the reporter molecule. By contrast, the quencher molecule's ability to quench the fluorescence of the reporter molecule in the second state is significantly smaller than in the first state. As a result, when the quencher molecule is converted from the first state to the second state, the ability of the quencher molecule to quench the reporter molecule is reduced, resulting in an increase in the average fluorescence intensity of reporter molecules on the probe.

Depending on the quencher molecule selected, the quencher may be converted from the first to the second state using a variety of different chemical reagents including enzymes. For example the conversion of the quencher molecule from the first state to the second state may involve a hydrolysis, peptide bond cleavage, phosphate bond cleavage, oxidation or reduction. Accordingly, the conversion may be performed using a chemical reagent capable of performing the hydrolysis, peptide bond cleavage, phosphate bond cleavage, oxidation or reduction. In one embodiment, the chemical reagent is an enzyme for which the quencher is a substrate, the enzyme catalyzing the conversion of the quencher molecule from the first state to the second state. For example, the enzyme may be a hydrolytic enzyme, a peptidase, a phosphorylase, an oxidase or a reductase.

In one embodiment, the first state of the quencher molecule is an oxidized state and the second state is a reduced state. When the quencher is in the oxidized state, the quencher molecule is able to quench the fluorescence of the reporter molecule. By contrast, the quencher molecule's ability to quench the fluorescence of the reporter molecule in the reduced state is significantly smaller than in the oxidized state. As a result, when the quencher molecule is reduced, i.e., changed from an oxidized state to a reduced state, the ability of the quencher molecule to quench the reporter molecule is reduced, resulting in an increase in the average fluorescence intensity of reporter molecules on the probe.

The present invention also relates to a method for monitoring a chemical reaction using a fluorescent probe according to the present invention. In the method, the fluorescence intensity of the reporter molecule on the probe is monitored as the probe is exposed to a reagent capable of converting the quencher from a first state to a second state. For example, when the reagent is a reducing agent or an enzyme having reducing activity, the quencher molecule is reduced from an oxidized state to a reduced state. The rate of increase in fluorescence is expected to be proportional to the amount of reagent present.

In one embodiment of the method, the reagent is an enzyme and the probe includes a quencher molecule which is a substrate for the enzyme, the enzyme converting the quencher from the first to the second state. According to the method, the probe is contacted with the enzyme. The fluorescence of the reporter molecule on the probe is monitored in order to detect the conversion of the quencher from the first to second states by the enzyme. Examples of types of enzymes which may be detected include hydrolytic enzymes, peptidases, phosphorylases, oxidases and reductases.

In another embodiment of the method, cell activation is monitored by measuring the ability of a sample of cells to convert a quencher molecule from a first state to a second state based on the presence of an enzyme indicative of viable cells. For example, the quencher molecule may be in an oxidized state and exposed to a sample of cells which, if viable, contains an enzyme capable of reducing the quencher molecule. As the quencher molecule is reduced by the enzyme, the average fluorescence intensity of the reporter molecules increases in proportion to the degree to which the quencher molecules have been reduced.

According to the probes and methods of the present invention, the quencher molecule is positioned on the probe relative to the reporter molecule such that the quencher is able to quench the fluorescence of the reporter molecule when the quencher is in the first state. In general, in order for a quencher molecule to quench an excited fluorophore, the quencher molecule must be within a minimum quenching distance of the excited reporter molecule at some time prior to the reporter molecule releasing the stored fluorescence energy. In one embodiment, the quencher molecule is positioned on the probe within about 10Å of the reporter molecule.

Figure 2:
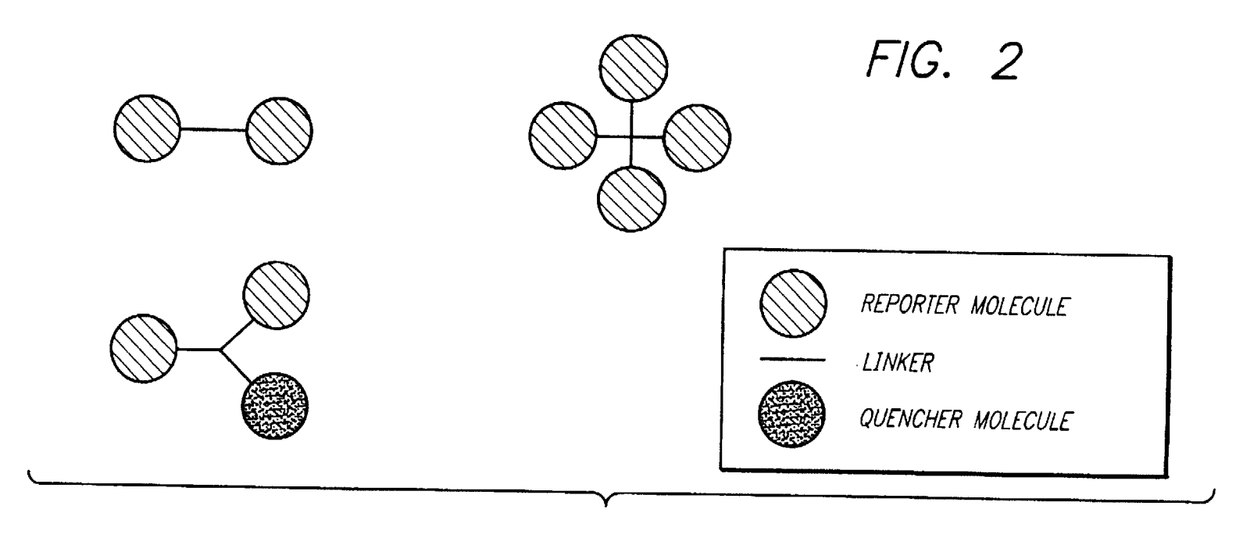
FIG. 2 illustrates a series of embodiments of the fluorescent probes of the present invention.

In one embodiment, the probe includes a single reporter molecule and a single quencher molecule. Alternatively, as illustrated by the different probes shown in FIG. 2, two or more reporter molecules and/or two or more quencher molecules can be linked to a probe. In yet another embodiment, more than one quencher molecule may be incorporated onto a probe per reporter molecule in order to increase the effectiveness of the quencher molecules to quench the reporter molecule(s) on the probe.

A wide variety of reporter molecules may be used in the probe and methods of the present invention. In general, the reporter molecule may be any molecule which is capable of generating a fluorescence signal and which is capable of being quenched by a quencher molecule.

The quencher molecules used in the probes of the present invention are capable being converted from a first state to a second state. In the first state, the quencher molecule is capable of absorbing the fluorescence energy of the excited reporter molecule. This generally involves the absorption band of the quencher molecule in the first state substantially overlapping the fluorescent emission band of the reporter molecule so that the quencher molecule is able to effectively quench the reporter molecule. In one embodiment, this is achieved by having the absorbance maximum of the quencher molecule be within about 150 nm of the absorbance maximum of the reporter molecule. The quencher molecules used in the probes are typically organic dyes, which may or may not be fluorescent, depending on the embodiment of the invention.

In one embodiment, the quencher molecules used in the probes of the present invention are capable of being reduced from an oxidized state to a reduced state. In the oxidized state, the quencher molecule is absorbs the fluorescence energy of the excited reporter molecule. In the reduced state, the quencher molecule has a lesser ability to quench the excited reporter molecule. An example of a quencher molecule having a lesser ability to quench an excited reporter molecule in a reduced state is dichloroindophenol (DCIP) methylene blue, and phenazine methosulfate. According to this embodiment, the quencher may be further characterized as being a substrate for a reductive enzyme. For example, dichloroindophenol is a blue colored, non-fluorescent dye which is a substrate for flavin containing, NADH-requiring enzymes, such as diaphorase.

In another embodiment, the quencher molecules used in the probes of the present invention are capable being converted from a first reduced state to a second oxidized state. In the oxidized first state, the quencher molecule is capable of absorbing the fluorescence energy of the excited reporter molecule. In the second oxidized state, the quencher molecule has a lesser ability to quench the excited reporter molecule. According to this embodiment, the quencher may be further characterized as being a substrate for an oxidative enzyme such as a peroxidase.

In another embodiment, the quencher molecules used in the probes of the present invention are capable of being hydrolyzed from a first state to a second, hydrolyzed state. In the first state, the quencher molecule absorbs the fluorescence energy of the excited reporter molecule. In the second, hydrolyzed state, the quencher molecule has a lesser ability to quench the excited reporter molecule. According to this embodiment, the quencher may be further characterized as being a substrate for a hydrolytic enzyme.

In yet another embodiment, the quencher molecules used in the probes of the present invention are capable of being converted from a first phosphorylated state to a second state where the phosphate group has been cleaved. In the phosphorylated state, the quencher molecule absorbs the fluorescence energy of the excited reporter molecule. In the second state, the quencher molecule has a lesser ability to quench the excited reporter molecule. According to this embodiment, the quencher may be further characterized as being a substrate for a phosphate bond cleaving enzyme such as a phosphorylase.

In yet another embodiment, the quencher molecules used in the probes of the present invention are capable of being converted from a first state in which a peptide or amino acid residue is attached to the quencher by an amide bond to a second state where the peptide or amino acid residue is cleaved leaving the quencher in a second state with an amine residue. In the first state, the quencher molecule absorbs the fluorescence energy of the excited reporter molecule. In the second state, the quencher molecule has a lesser ability to quench the excited reporter molecule. According to this embodiment, the quencher may be further characterized as being a substrate for a peptidase.

There is a great deal of guidance available in the literature for selecting reporter-quencher pairs, as exemplified by the following references: Clegg, Meth. Enzymol., 211: 353–388 (1992); Wo, et al., Anal. Biochem., 218: 1–13 (1994); Pesce et al., editors, Fluorescence Spectroscopy (Marcel Dekker, New York, 1971); White et al., Fluorescence Analysis: A Practical Approach (Marcel Dekker, New York, 1970); and the like. The literature also includes references providing exhaustive lists of fluorescent and chromogenic molecules and their relevant optical properties for choosing reporter-quencher pairs, e.g., Beriman, Handbook of Fluorescence Spectra of Aromatic Molecules, 2nd Edition (Academic Press, New York, 1971); Griffiths, Colour and Constitution of Organic Molecules (Academic Press, New York, 1976); Bishop, editor, Indicators (Pergamon Press, Oxford, 1972); Haugland, Handbook of Fluorescent Probes and Research Chemicals (Molecular Probes, Eugene, 1992) Pringsheim, Fluorescence and Phosphorescence (Interscience Publishers, New York, 1949); and the like. Further, there is extensive guidance in the literature for derivatizing reporter and quencher molecules for covalent attachment via common reactive groups that can be added to an oligonucleotide, as exemplified by the following references: Haugland, Handbook of Fluorescent Probes and Research Chemicals (Molecular Probes, Eugene, 1992) Pringsheim, Fluorescence and Phosphorescence (Interscience Publishers, New York, 1949); Ullman et al., U.S. Pat. No. 3,996,345; Khanna et al., U.S. Pat. No. 4,351,760; and the like.

A wide variety of linkers may be used to link the quencher molecule to the reporter molecule. Examples of linkers which may be used in the probes of the present invention include alkyl groups, glycols, ethers, polyethers, polyamides, polyesters, polynucleotides and polypeptides. More specific examples of suitable linkers include $C_{4-30}$alkyls, $C_{4-30}$ glycols, $C_{4-30}$ ethers, $C_{4-30}$ polyethers and polynucleotides and polypeptides having between 4 and 60 bases.

The reporter molecule and quencher molecule should be positioned on the linker such that the quencher molecule is within a minimum quenching distance of the excited reporter molecule at some time prior to the reporter molecule releasing the stored fluorescence energy. In one embodiment, the reporter molecule and/or the quencher molecule is positioned at a terminal end of the linker. In another embodiment, both the reporter and quencher molecules are positioned at terminal ends of the linker.

In the method for monitoring chemical reactions using a probe according to the present invention, a probe including a quencher molecule in a first state is exposed to a reagent which is capable of converting the quencher into a second state. The fluorescence intensity of the reporter molecule is monitored over time. As the reagent converts quencher molecules to the second state, more and more reporter molecules are not quenched by the quencher molecules. As a result of the decreased quenching, the fluorescence intensity of the reporter molecule increases, indicating the occurrence of the chemical reaction being monitored.

The method of the present invention may be used to fluorescently monitor the presence of any type of reagent which is capable of converting a quencher molecule from a first higher quenching state to second lower quenching state. The method may also be used to fluorescently monitor the generation of reagents capable of converting the quencher molecule from the first to the second states. For example, the probes of the present invention may be used in this method to fluorescently monitor the generation of a byproduct from a chemical process and thus serve as a chemical sensor for the generation of the byproduct. The method may also be used to quantify the presence of reagents capable of converting the quencher molecule from the first to the second state.

In one embodiment of the method, the presence of a reducing agent is monitored. According to this embodiment of the method, the probe includes an oxidized quencher molecule which is reduced by the reducing agent. As the reducing agent reduces the oxidized quencher, more and more reporter molecules are not quenched. As a result of the decreased amount of quenching, the fluorescence intensity of the reporter molecule increases, indicating the reduction of the quencher molecule.

In another embodiment, the method is used to monitor enzymatic chemical reactions and thus can be used to detect for and quantify enzyme activity. According to this embodiment, the probe includes an quencher molecule which is a substrate for the enzyme being detected. For example, the probe can include an oxidized quencher molecule which is a substrate for the enzyme being detected. For example, the enzyme may be a flavin containing, NADH-requiring enzyme, such as diaphorase. Accordingly, the quencher may be a substrate for the flavin containing, NADH-requiring enzyme, such as dichloroindophenol (DCIP).

The method for monitoring enzymatic chemical reactions can also be used to detect for and quantify cell activation. According to this embodiment of the method, the probe includes a quencher molecule which is a substrate for an enzyme present in viable cells. The probe is contacted with a sample of cells and the fluorescence intensity of the reporter molecule is monitored. As the quencher molecule is converted to a second state having less quenching ability, the fluorescence intensity of the reporter molecules increases. In one embodiment, the probe includes an oxidized quencher molecule which is a substrate for an enzyme having reductive activity which is present in viable cells. For example, the enzyme may be a flavin containing, NADH-requiring enzymes, such as diaphorase. The probe is contacted with a sample of cells and the fluorescence intensity of the reporter molecule is monitored. As the quencher molecule is reduced, the fluorescence intensity of the reporter molecules increases in proportional to the concentration of activated cells.

The probes and methods of the present invention are illustrated by the following examples. Further objectives and advantages other than those set forth above will become apparent from the examples and accompanying drawings.

EXAMPLES

The following example details the synthesis of DCIP-FI, a reductive, energy-transfer fluorogenic probe which shows enhanced fluorescence after enzymatic reduction. Unlike prior art fluorogenic probes, the fluorescence of DCIP-FI can be altered by enzymatic modification of the quencher molecule as opposed to cleavage of the quencher molecule from the probe.

The quencher molecule used in this example is dichloroindephenol (DCIP), a blue-colored, non fluorescent dye which is a substrate for flavin-containing, NADH-requiring enzymes. Upon reduction it becomes colorless. Before reduction it acts as a quencher for dyes which emit at wavelengths shorter that DCIP (650 nm). In this example, DCIP-FI is shown to be a substrate for diaphorase and exhibits an almost 4-fold enhancement of fluorescence after reduction.

silica gel with 1:1 ethyl acetate:hexane showed complete conversion of the starting acid to a fluorescent, lower rf product.

Scheme 1

Preparation of DCIP-FI

As illustrated in Scheme 2 below, 5-carboxyfluorescein succinimidyl ester (0.9 µmol), 1-5-diaminopentane (0.9 µmol), dimethylformamide (50 µL) and 3-hydroxybenzoic acid, succinimidyl ester (0.9 µmol) were combined.

DCIP-FI

Preparation of 3-hydroxybenzoic acid, succinimidyl ester

As illustrated in Scheme 1 below, 1,3-dicyclohexylcarbodiimide (82 mg, 0.40 mmol) was added to a solution of 3-hydroxybenzoic acid (50 mg, 0.36 mmol) and N-hydroxysuccinimide (46 mg, 0.40 mmol) in ethyl acetate (1 mL). After 1 minute, crystals of dicyclohexylurea appeared. The next day, acetic acid (20 µL) was added. The mixture was filtered through glass wool, washed with dilute HCl (1N) and dried over $Na_2SO_4$. The solution was concentrated to a white solid. Thin layer chromatography on Bicarbonate/carbonate buffer (1M, pH 9, 50 µL) was added. The solution turned bright orange. 2,6 Dichloroquinone-4-chlorimide (Gibb's Reagent, 4 mmol) was added.

Analysis of the solution with an HPLC equipped with a diode array absorbance spectrophotometer using reverse-phase column and continuous gradient of 10% to 30% acetonitrile vs 0.1M triethylammonium acetate showed a new compound which contained both fluorescein (abs max= 490 nm) and carboxydichloroindophenol (abs max=640 nm). A portion of the reaction (5 µL) was injected and the fraction eluting at 16 minutes (DCIP-FI) was collected.

Scheme 2

Reaction of DCIP-Fl with NADH and diaphorase

As illustrated in Scheme 3 below, DCIP-Fl was reduced by diaphorase in the presence of NADH cofactor. More specifically, solutions of NADH (5 mg/mL) and diaphorase (approx. 1 mg/ 5 mL) in PBS were prepared. The solution of DCIP-Fl was used directly from the HPLC (9 µM). A solution containing PBS (300 µL), DCIP-Fl (50 µL) and NADH (10 µL) was measured by absorbance and fluorescence (460 nm excitation). Diaphorase (10 µL) was added and the absorbance and fluorescence measured.

Scheme 3

Figure 3:
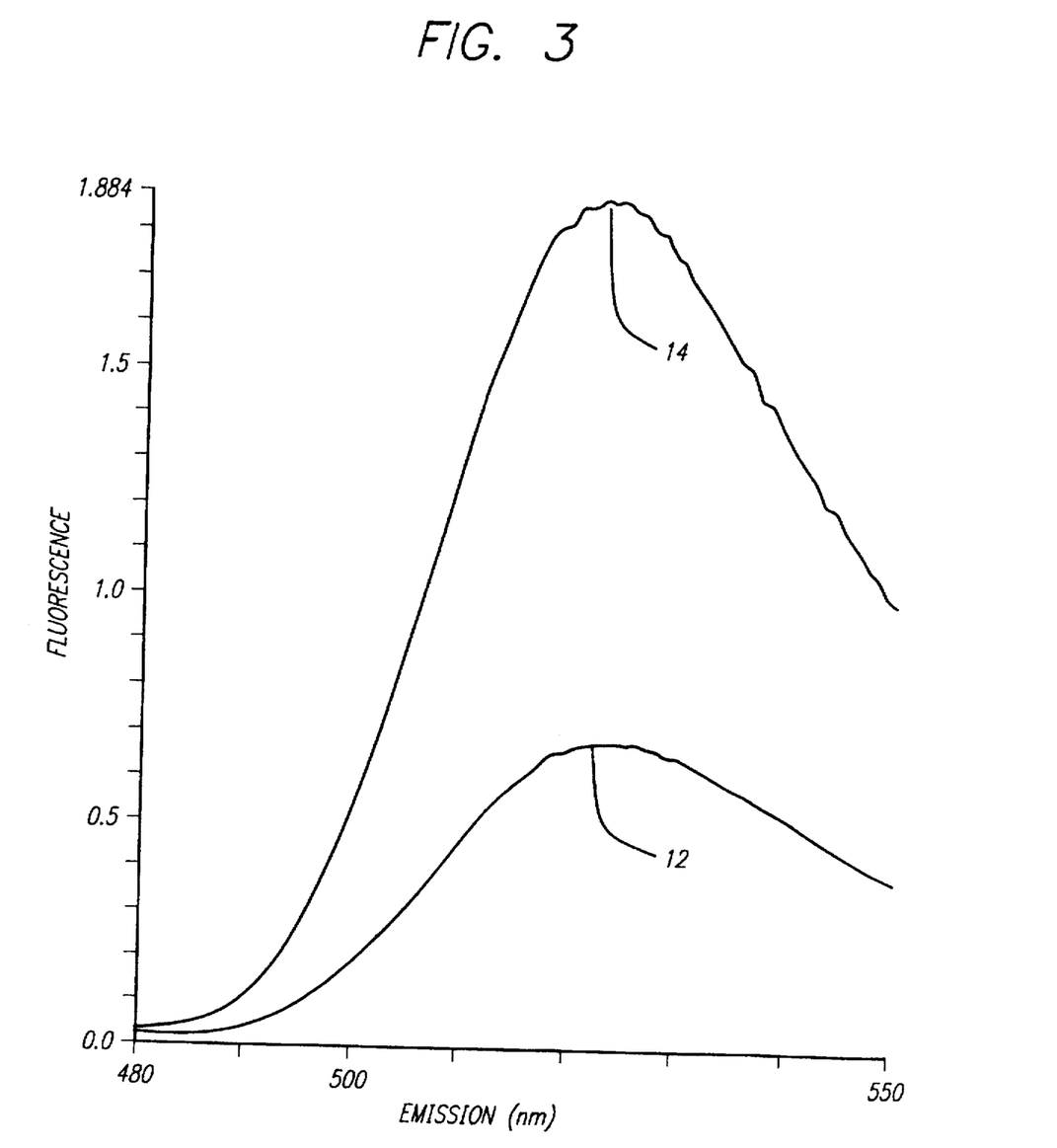
FIG. 3 is a plot of the fluorescence of the DCIP-Fl probe before and after being contacted with diaphorase.
Figure 4A:
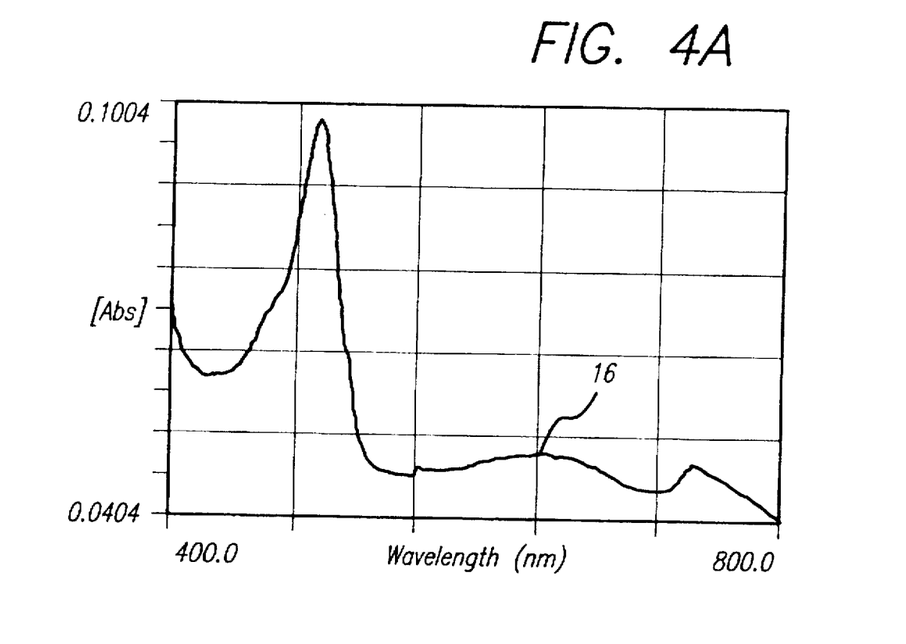
FIG. 4A is a plot of the absorbance of the DCIP-Fl probe before being contacted with diaphorase.
Figure 4B:
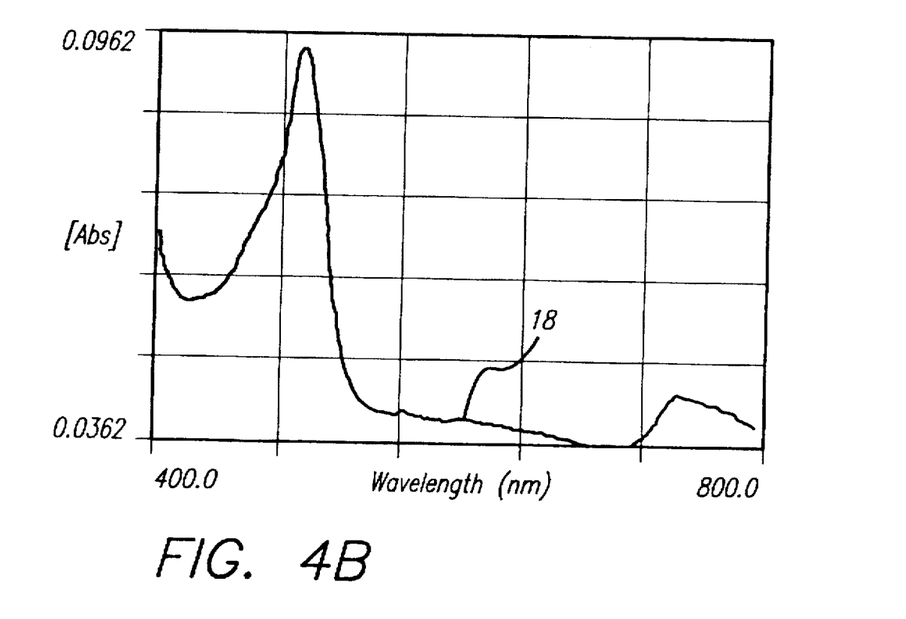
FIG. 4B is a plot of the absorbance of the DCIP-Fl probe after being contacted with diaphorase.

FIG. 3 is a plot of the fluorescence of the DCIP-FI probe before (12) and after (14) being contacted with diaphorase. FIG. 4A is a plot of the absorbance of the DCIP-FI probe 16 before being contacted with diaphorase. FIG. 4B is a plot of the absorbance of the DCIP-FI probe 18 after being contacted with diaphorase. As illustrated in FIG. 3, the fluorescence of the DCIP-Fl probe at about 520 nm increases by a factor of about 4 after being contacted with diaphorase. Meanwhile, as illustrated in FIGS. 4A and 4B, the absorbance of DCIP decreases after being contacted with diaphorase, indicating the reduction of DCIP.

While the present invention is disclosed by reference to the embodiments and examples detailed above, it is to be understood that these examples are intended in an illustrative rather than limiting sense, as it is contemplated that modifications will readily occur to those skilled in the art, which modifications will be within the spirit of the invention and the scope of the appended claims.

What is claimed is:

1. A method for fluorescently detecting a reagent in a sample comprising the steps of:

contacting a fluorescent probe including a reporter molecule and a quencher molecule with a sample containing a reagent, the quencher molecule being converted by the reagent from a first state which quenches the fluorescence of the reporter molecule to a second state which has a reduced ability to quench the reporter molecule, the reporter molecule and quencher molecule having absorbance maxima and the absorbance maximum of the quencher molecule being within about 150 nm of the absorbance maximum of the reporter molecule; and monitoring the fluorescence intensity of the reporter molecule as the quencher molecule is converted from the first state to the second state by the reagent.

2. A method for fluorescently detecting a reagent in a sample comprising the steps of:

contacting a fluorescent probe including a reporter molecule and a quencher molecule with a sample containing a reagent, the quencher molecule being converted by the reagent from a first state which quenches the fluorescence of the reporter molecule to a second state which has a reduced ability to quench the reporter molecule, wherein the quencher molecule has an absorbance maximum between about 600 and 700 nm; and monitoring the fluorescence intensity of the reporter molecule as the quencher molecule is converted from the first state to the second state by the reagent.

3. The method according to claim 1 wherein the absorbance maximum of the quencher molecule is within about 30 nm of the absorbance maximum of the reporter molecule.

4. The method according to claim 1 wherein the probe further including a linker for linking the reporter molecule to the quencher, the linker being selected from the group consisting of alkyl groups, glycols, ethers, polyethers, polynucleotides and polypeptides.

5. A method for fluorescently detecting a reagent in a sample comprising the steps of:

contacting a fluorescent probe including a reporter molecule and a quencher molecule with a sample containing a reagent, the quencher molecule being converted by the reagent from a first state which quenches the fluorescence of the reporter molecule to a second state which has a reduced ability to quench the reporter molecule, wherein the quencher is selected from the group consisting of dichloroindophenol, methylene blue and phenazine methosulfate; and monitoring the fluorescence intensity of the reporter molecule as the quencher molecule is converted from the first state to the second state by the reagent.

6. A method for fluorescently detecting a reagent in a sample comprising the steps of:

contacting a fluorescent probe including a reporter molecule and a quencher molecule with a sample containing a reagent, the quencher being converted by the reagent from a first state which quenches the fluorescence of the reporter molecule to a second state which has a reduced ability to quench the reporter molecule, wherein the quencher is dichloroindophenol; and monitoring the fluorescence intensity of the reporter molecule as the quencher molecule is converted from the first state to the second state by the reagent.

7. A method for fluorescently detecting a reagent in a sample comprising the steps of:

contacting a fluorescent probe including a reporter molecule and a quencher molecule with a sample containing a reagent, the quencher molecule being converted by the reagent from a first state which quenches the fluorescence of the reporter molecule to a second state which has a reduced ability to quench the reporter molecule, wherein the probe includes at least two quencher molecules and monitoring the fluorescence intensity of the reporter molecule as the quencher molecule is converted from the first state to the second state by the reagent.

8. A method for fluorescently detecting a reagent in a sample comprising the steps of:

contacting a fluorescent probe including a reporter molecule and a quencher molecule with a sample containing a reagent, the quencher molecule being converted by the reagent from a first state which quenches the fluorescence of the reporter molecule to a second state which has a reduced ability to quench the reporter molecule, wherein the probe includes at least one reporter molecule and at least one quencher molecule and where the ratio of quencher molecules to reporter molecules on the probe is at least 2:1; and monitoring the fluorescence intensity of the reporter molecule as the quencher molecule is converted from the first state to the second state by the reagent.

9. A method for fluorescently detecting enzyme activity comprising the steps of:

contacting a fluorescent probe including a reporter molecule and a quencher molecule with a sample containing an enzyme, the quencher molecule being converted by the enzyme from a first state which quenches the fluorescence of the reporter molecule to a second state which has a reduced ability to quench the reporter molecule, wherein the quencher is selected from the group consisting of dichloroindophenol, methylene blue and phenazine methosulfate; and monitoring the fluorescence intensity of the reporter molecule as the quencher molecule is converted from the first state to the second state by the enzyme.

10. The method according to claim 9 wherein the reagent is an enzyme and the quencher molecule is a substrate for the enzyme.

11. The method according to claim 10 wherein the enzyme reduces the quencher molecule from a first oxidized state to a second reduced state.

12. The method according to claim 10 wherein the enzyme oxidizes the quencher molecule from a first reduced state to a second oxidized state.

13. The method according to claim 10 wherein the enzyme hydrolyzes the quencher molecule from a first state to a second hydrolyzed state.

14. The method according to claim 10 wherein the enzyme is a peptidase and the quencher includes an amide in the first state which is converted by the peptidase to an amine.

15. The method according to claim 10 wherein the enzyme is a phosphorylase, the quencher including a phosphate group in the first state which is cleaved by the phosphorylase.

16. The method according to claim 9 wherein the conversion of the probe from the first state to the second state involves a reaction selected from the group consisting of reduction, oxidation, hydrolysis, phosphate cleavage, and the conversion of an amide to an amine.

17. A method for fluorescently detecting enzyme activity comprising the steps of:

contacting a fluorescent probe including a reporter molecule and a quencher molecule with a sample containing an enzyme, the quencher molecule being converted by the enzyme from a first state which quenches the fluorescence of the reporter molecule to a second state which has a reduced ability to quench the reporter molecule, wherein the quencher is dichloroindophenol; and monitoring the fluorescence intensity of the reporter molecule as the quencher molecule is converted from the first state to the second state by the enzyme.

18. A fluorescent probe comprising:

a fluorescent reporter molecule; and a quencher molecule positioned on the probe relative to the reporter molecule such that the quencher molecule quenches the fluorescence of the reporter molecule when in a first state, the quencher molecule being a substrate for an enzyme which converts the quencher molecule to a second state which has a reduced ability to quench the reporter molecule, the quencher molecule and the reporter molecule having absorbance maxima, the absorbance maximum of the quencher molecule being within about 150 nm of the absorbance maximum of the reporter molecule.

19. The probe according to claim 18 wherein the quencher molecule is a substrate for an enzyme which reduces the quencher from a first oxidized state to a second reduced state.

20. The probe according to claim 18 wherein the quencher molecule is a substrate for an enzyme which oxidizes the quencher molecule from a first reduced state to a second oxidized state.

21. The probe according to claim 18 wherein the quencher molecule is a substrate for an enzyme which hydrolyzes the quencher molecule from a first state to a second hydrolyzed state.

22. The probe according to claim 18 wherein the quencher includes an amide in the first state which is converted by a peptidase to an amine.

23. The probe according to claim 18 wherein the quencher includes a phosphate group in the first state, the quencher molecule being a substrate for an enzyme which cleaves the phosphate group.

24. A fluorescent probe comprising:

a fluorescent reporter molecule; and a quencher molecule positioned on the probe relative to the reporter molecule such that the quencher molecule quenches the fluorescence of the reporter molecule when in a first state, the quencher molecule being a substrate for an enzyme which converts the quencher molecule to a second state which has a reduced ability to quench the reporter molecule, wherein the quencher molecule has an absorbance maximum between about 600 and 700 nm.

25. The probe according to claim 18 wherein the absorbance maximum of the quencher molecule is within about 30 nm of the absorbance maximum of the reporter molecule.

26. The probe according to claim 18 further including a linker for linking the reporter molecule to the quencher, the linker being selected from the group consisting of alkyl groups, glycols, ethers, polyethers, polynucleotides and polypeptides.

27. A fluorescent probe comprising:

a fluorescent reporter molecule; and a quencher molecule positioned on the probe relative to the reporter molecule such that the quencher molecule quenches the fluorescence of the reporter molecule when in a first state, the quencher molecule being a substrate for an enzyme which converts the quencher molecule to a second state which has a reduced ability to quench the reporter molecule, wherein the quencher is selected from the group consisting of dichloroindophenol, methylene blue and phenazine methosulfate.

28. A fluorescent probe comprising:

a fluorescent reporter molecule; and a quencher molecule positioned on the probe relative to the reporter molecule such that the quencher molecule quenches the fluorescence of the reporter molecule when in a first state, the quencher molecule being a substrate for an enzyme which converts the quencher molecule to a second state which has a reduced ability to quench the reporter molecule, wherein the quencher is dichloroindophenol.

29. A fluorescent probe comprising:

a fluorescent reporter molecule; and a quencher molecule positioned on the probe relative to the reporter molecule such that the quencher molecule quenches the fluorescence of the reporter molecule when in a first state, the quencher molecule being a substrate for an enzyme which converts the quencher molecule to a second state which has a reduced ability to quench the reporter molecule, wherein the probe includes at least two quencher molecules.

30. A fluorescent probe comprising:

a fluorescent reporter molecule; and a quencher molecule positioned on the probe relative to the reporter molecule such that the quencher molecule quenches the fluorescence of the reporter molecule when in a first state, the quencher molecule being a substrate for an enzyme which converts the quencher molecule to a second state which has a reduced ability to quench the reporter molecule, wherein the probe includes at least one reporter molecule and at least one quencher molecule and where the ratio of quencher molecules to reporter molecules on the probe is at least 2:1.

* * * * *

UNITED STATES PATENT AND TRADEMARK OFFICE
CERTIFICATE OF CORRECTION

PATENT NO. : 5,795,729
DATED : Aug. 18, 1998
INVENTOR(S) : Linda G. Lee

It is certified that error appears in the above-indentified patent and that said Letters Patent is hereby corrected as shown below:

Title page, under References Cited, FOREIGN PATENT DOCUMENTS, add the following two cites:
"0601889 A2    6/1994   European Pat. Off.", and
"WO 03446    4/1990   PCT".

Column 15, claim 7, line 32, after "molecules", add --;--.

Signed and Sealed this

Ninth Day of February, 1999

Attest:

Attesting Officer

*Acting Commissioner of Patents and Trademarks*